United States Patent [19]

Lutz et al.

[11] Patent Number: 4,995,903
[45] Date of Patent: Feb. 26, 1991

[54] ALKYL-, ALKENYL- AND ALKYNYLNITROGUANIDINES AS CYTOKININ PLANT GROWTH REGULANTS

[75] Inventors: Albert W. Lutz, Princeton, N.J.; Shirley J. Rodaway, Newtown, Pa.

[73] Assignee: American Cyanamid Company, Stamford, Conn.

[21] Appl. No.: 275,165

[22] Filed: Nov. 23, 1988

Related U.S. Application Data

[62] Division of Ser. No. 23,348, Mar. 9, 1987, Pat. No. 4,822,408, which is a division of Ser. No. 759,705, Jul. 29, 1985, Pat. No. 4,667,226.

[51] Int. Cl.$^5$ ............................................. A01N 33/02
[52] U.S. Cl. ....................................................... 71/121
[58] Field of Search ........................... 71/121; 426/321

[56] References Cited

U.S. PATENT DOCUMENTS

| | | | |
|---|---|---|---|
| 2,538,907 | 1/1951 | McKay | 564/108 |
| 2,946,820 | 7/1960 | Henry et al. | 564/108 |
| 3,035,094 | 5/1962 | Hageman | 564/108 |
| 4,594,092 | 6/1986 | Speltz et al. | 71/121 |
| 4,677,226 | 6/1987 | Lutz et al. | 564/108 |
| 4,804,780 | 2/1989 | Speltz et al. | 564/104 |

FOREIGN PATENT DOCUMENTS 3345281 12/1982 Fed. Rep. of Germany .

OTHER PUBLICATIONS

Lowe et al., Journal of Organic Chemistry, vol. 28 pp. 1496–1498.

Primary Examiner—Richard L. Raymond
Assistant Examiner—Brian Bembenick
Attorney, Agent, or Firm—Alice C. Brennan

[57] ABSTRACT

There are provided novel branched alkenylnitroguanidine compounds. A method for inducing cytokinin plant growth regulant activity in crop plants by applying to the crop plants certain alkyl-, alkenyl- and alkynyl-nitroguanidine compounds is provided.

4 Claims, No Drawings

ALKYL-, ALKENYL- AND ALKYNYLNITROGUANIDINES AS CYTOKININ PLANT GROWTH REGULANTS

This is a continuation of application, Ser. No. 023,348, filed Mar. 9, 1987, now U.S. Pat. No. 4,822,408, issued Apr. 18, 1989, which is a division of Ser. No. 06/759,705 now U.S. Pat. No. 4,677,226, which issued on June 30,1987.

BACKGROUND OF THE INVENTION

This invention relates to certain novel alkenylnitroguanidine compounds. It also relates to a method for inducing cytokinin plant growth regulant responses in crop plants by applying to said crop plants an effective amount of an alkyl-, alkenyl- or alkynylnitroguanidine compound.

Although certain phenyl and benzylnitroguanidines are disclosed by L. M. Speltz et al. in an American Cyanamid Patent Application, Publication Number DE 3345-281 -A1; 84-159658/26, Dec. 20, 1982, said disclosure describes only phenyl and benzylnitroguanidines and phenyl and benzylcyanoguanidines as yield enhancing agents for crops, antilodging agents for grains such as rice and a novel class of cytokinins. The Speltz et al. application does not suggest that other nitroguanidines or cyanoguanidines would exhibit any or all of the above biological activities. Moreover, it fails to disclose or suggest the novel alkenylnitroguanidines of the present invention or to indicate that such compounds would be useful in the clonal propagation of plants.

SUMMARY OF THE INVENTION

The novel alkenylnitroguanidine compounds of this invention may be represented by

$$\text{RNHCNHNO}_2 \quad \overset{\text{NH}}{\|} \tag{I}$$

where R is a branched $C_2$–$C_6$ alkenyl substituent optionally substituted with from one to three, and preferably one or two OH, halogen or $C_1$–$C_3$ alkoxy groups, and the salts, geometric isomers, optical isomers and tautomers thereof.

The present invention also relates to a method for inducing cytokinin responses in plants by applying to the foliage of said plants or to soil containing seeds or other propagating organs thereof, an effective amount of an alkyl-, alkenyl- or alkynylnitroguanidine compound. The compounds suitable for this invention are represented by

$$\text{R}^1\text{NHCNHNO}_2 \quad \overset{\text{NH}}{\|} \tag{II}$$

wherein $R^1$ is $C_1$–$C_6$ alkyl, optionally substituted with from one to three, and preferably one or two, OH, halogen or $C_1$–$C_3$ alkoxy substituents; $C_2$–$C_6$ *alkenyl optionally substituted with from one to three, and preferably one or two OH, halogen or $C_1$–$C_3$ alkoxy substituents* or $C_2$–$C_6$ alkynyl optionally substituted with one to three, and preferably one or two, OH, halogen or $C_1$–$C_3$ alkoxy substituents; and the salts geometric isomers, optical isomers and tautomers thereof.

Surprisingly, it has been found that the alkyl-, alkenyl- and alkynylnitroguanidines of this invention provide an improved method for assisting in the in vitro clonal propagation of plants. The alkyl-, alkenyl- and alkynylnitroguanidines of the invention also provide a means for asexually reproducing genetically similar plants and thus a means for the rapid multiplication of new cultivars, possessing improved or differing characteristics.

PREFERRED EMBODIMENT OF THE INVENTION

As cytokinins, the Formula I and II, alkylnitroguanidines, alkenylnitroguanidines and alkynylnitroguanidines produce enhanced growth effects on translocation, with enhanced chlorophyll biosynthesis in some tissues or decreased chlorophyll degradation (senescence) in others.

A preferred group of Formula II compounds for use as cytokinins have the above formula wherein $R^1$ is $C_3$–$C_6$ alkyl, optionally substituted with one or two OH, halogen or $C_1$–$C_3$ alkoxy; $C_4$–$C_6$ alkenyl, optionally substituted with one or two OH, halogen or $C_1$–$C_3$ alkoxy or $C_4$–$C_6$ alkynyl, optionally substituted with one or two OH, halogen or $C_1$–$C_3$ alkoxy groups.

Salts of the alkyl-, alkenyl- or alkynylnitroguanidine for inducing cytokinin responses in plants when applied in accordance with the method of the present invention, include the inorganic alkali metal, alkaline earth metal, Co, Cu, Zn, and Ag salts, together with the organic amine salts represented by structure, $N^+R_aR_bR_cR_d$, wherein $R_a$, $R_b$, $R_c$, and $R_d$ are each selected from hydrogen and alkyl $C_1$–$C_{30}$ straight or branched chain and optionally substituted with one or two -OH, $C_3$–$C_6$ alkenyl or $C_3$–$C_6$ alkynyl groups. Preferred salts of these compounds include the sodium, calcium, magnesium, potassium, ammonium, methylamine, trimethylamine, dodecylamine, tributylamine, diisopropylamine, triethylamine, tetrabutylamine, and tallow-amine salts.

These salts are readily prepared by dissolving or dispersing the appropriate compound as depicted by Formula II above in an aqueous solution or suspension of, for example, an alkali metal hydroxide, alkaline earth metal hydroxide or organic ammonium hydroxide.

When applying the nitroguanidines of the present invention to foliage of growing crops or the soil in which they have been planted, the formulated compounds are applied to provide about 0.05 kg/ha to about 8.0 kg/ha and preferably about 0.25 kg/ha to 4.0 kg/ha of the alkyl-, alkenyl- or alkynylnitroguanidine.

The compounds of the present invention are effective substitutes for the extensively investigated cytokinin, $N^6$-benzyladenine, in promoting growth of cytokinin dependent soybean callus in tissue culture. Additionally, the cucumber cotyledon bioassay has also been used to demonstrate the cytokinin like activity obtained with the compounds of the invention. As with many hormonetype bioassays, the response is log linear with respect to concentration of compound required to elicit a response.

It is contemplated that the compounds of the present invention will be useful for the treatment of fresh, green fruits and vegetables, ornamental foliage, and fresh, green, newly harvested livestock feed such as alfalfa, sorghum and corn silage, to increase their resistance to deterioration and preserve the color thereof. For use in this treatment the alkyl-, alkenyl or alkynylnitroguanidines of this invention can be formulated as liquid or solid compositions which may be dispersed in a liquid or solid diluent for application to the foliage of the plants, or to the soil in which they are grown. The substituted guanidines of the invention may be formulated as flowable concentrates, emulsifiable concentrates, wettable powders, dusts or dust concentrates. Aqueous sprays containing from about 0.01 to 1000 ppm of alkyl-, alkenyl- or alkynylnitroguanidine are effective for this invention.

A typical emulsifiable concentrate can be prepared by dissolving, on a weight basis, about 8% of the alkyl-, alkenyl- or alkynylnitroguanidine in about 40% of N-methylpyrrolidone, about 35% of a mixture of substituted benzenes, and about 10% of a spreader activator, containing alkylarylpolyoxyethylene glycol, free fatty acid and propanol, with about 7% by weight of a non-ionic surfactant, such as octylphenoxy polyethoxy ethanol or nonylphenoxy polyethoxy ethanol. This concentrate may be dispersed in water for application as a dilute liquid spray.

Emulsifiable concentrates can also be prepared by dissolving, on a weight basis, about 10% of the active guanidine in about 58% of N-methylpyrrolidone, about 24% octyl alcohol, and about 8% polyoxyethylated castor oil.

Flowable liquid concentrates can be prepared by grinding together about 35%, by weight, of the nitroguanidine, about 0.40% colloidal magnesium aluminum silicate, about 1.50% sodium salts of polymerized alkyl naphthalene sulfonic acids, about 8.0% propylene glycol, about 0.1% ethoxylated octylphenol, about 0.1% nonylphenoxy polyethoxy ethanol, about 0.07% citric acid, about 0.06% xanthan gum, about 0.10% paraformaldehyde and about 54.77% water.

Flowable liquid concentrates can also be prepared by milling together about 43%, by weight, of the nitroguanidine with about 0.4%, by weight, of colloidal magnesium aluminum silicate, about 1.5%, by weight, of naphthalene formaldehyde condensate, about 8%, by weight, of polyethylene glycol, about 0.1%, by weight, of nonylphenol ethylene oxide condensate (9–11 moles ethylene oxide), about 0.1%, by weight, of a dispersing agent (e.g., sodium lignosulfonate), about 0.07%, by weight, citric acid, about 49%, by weight, of water, and about 0.06%, by weight, of xanthan gum. This concentrate is dispersed in water for application as a liquid spray.

A typical wettable powder can be prepared by grinding together, on a weight basis, about 20 to 45% of a finely-divided carrier (e.g., kaolin, bentonite, diatomaceous earth and attapulgite, about 45 to 80% of the alkyl or alkenylnitroguanidine, about 2 to 5% of a dispersing agent (e.g., sodium lignosulfonate), and about 2 to 5% of a nonionic surfactant (e.g., octylphenoxy polyethoxy ethanol or nonylphenoxy polyethoxy ethanol). This formulation is generally dispersed in water for application as a liquid spray.

Advantageously, the alkyl-, alkenyl- and alkynylnitroguanidines encompassed by Formulas I and II are useful in the methods of the present invention and can be prepared by reaction of an appropriately substituted aniline with approximately an equimolar amount of an N-alkyl-N-nitroso-N'-nitroguanidine in the presence of an aqueous alcoholic solution. The mixture is heated to about 40° C., treated with a strong base such as sodium hydroxide, and the alcohol removed from the mixture by evaporation. The remaining liquid is then filtered, and the filtrate acidified with a strong mineral acid (i.e., hydrochloric acid) to yield the desired nitroguanidine. This reaction is graphically illustrated as follows:

$R^1NH_2$ +

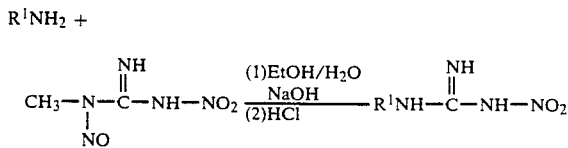

wherein $R^1$ is alkyl $C_1$–$C_6$, alkenyl $C_2$–$C_6$ or alkynl $C_2$–$C_6$ and each of said alkyl, alkenyl or alkynyl function is straight or branched and each is optionally substituted with halogen, OH or alkoxy $C_1$–$C_3$ groups.

Nutrient media suitable for use in the in vitro propagation of plants may comprise a mixture of various mineral salts, vitamins, amino acids, a carbohydrate source, and biological agents and hormones such as gibberellins and auxins, depending upon the cultivar or plant species which is being propagated. For example, it is a well known phenomenon that both embryogenesis and shoot/root induction depend on both the levels and ratios of auxins and cytokinins in the inductive medium. The cultivar or plant species is of course an important factor to consider in that certain species, cultivars, individuals or plant parts are capable of producing some of the necessary factors even while in tissue culture. A semisolid supporting medium such as agar or an aqueous medium may be used. When auxins are used in the inductive medium they usually must be present at relatively low levels to allow expression of the embryo and shoot inducing phenomena.

The preferred concentration of Formula I and Formula II compounds for use in the in vitro propagation of plants are on the order of $10^{-5}$ to $10^{-4}$ moles per liter of compound. These concentrations are dependent on factors such as the species or cultivar employed, the origin of the tissue to be propagated, and additional components in the medium. With certain of the compounds, primarily those which have activity at low concentrations, the use of the high concentrations may be deleterious to subsequent shoot or embryo development and should be avoided. Such a phenomenon is often seen when hormones or hormone-substitutes are employed by biological systems.

The following examples are presented for the purpose of illustrating the present invention and facilitating a better understanding thereof.

EXAMPLE 1 1

Preparation of 1-(3-methyl-2-butenyl)-3-nitroguanidine 3-methyl-2-butenylamine (3.0 g) is added dropwise at room temperature to a slurry of 1-methyl-3-nitro-1-nitrosoguanidine (4.3 g) in 50 ml of EtOH/H$_2$O (1/1). After stirring the mixture at room temperature for 18 hours, the precipitate which forms is removed by filtration. The solid is then slurred with dilute hydrochloric acid, collected by filtration and washed with ethanol/water (30/70). Recrystallization from ethanol gives a white solid with mp 134°–136° C.

Following the above procedure but substituting the appropriate amine for 3-methyl-2-butenyl amine yields the compounds listed in Table I below. The reaction may be illustrated as shown in Table I.

TABLE 1

$$RNH_2 + CH_3-\underset{\underset{NO}{|}}{N}-\overset{\overset{NH}{\|}}{C}-NH-NO_2 \xrightarrow{EtOH/H_2O} RNHCNHNO_2\;(NH)$$

| R | MP °C. |
|---|---|
| n-C$_5$H$_{11}$— | 101–102 |
| CH$_2$=CHCH$_2$— | 110–112 |
| C$_2$H$_5$OCH$_2$CH$_2$— | 86.5–88.5 |
| (CH$_3$)$_2$CHCH$_2$CH$_2$— | 145–148 |
| ClC(CH$_3$)=CHCH$_2$— (Z) | 124–127 |
| n-C$_4$H$_9$— | 86.0–87.5 |
| HC≡C—C(CH$_3$)$_2$— | 112–113 |
| CH$_3$OCH$_2$CH(CH$_3$)— | 101–104 |
| (CH$_3$)$_2$CH— | 158–160 |
| C$_2$H$_5$C(CH$_3$)$_2$— | 137.5–139 |
| CH$_2$=CHC(CH$_3$)$_2$— | 122.5–123.5 |
| HOCH$_2$CH(CH$_3$)CH$_2$— | 116–121 |
| HOCH$_2$CH$_2$CH$_2$CH$_2$— | 113–116 |
| Cl$_2$C=CHCH$_2$CH$_2$— | 134–136 |
| (HOCH$_2$)(CH$_3$)C=CH(CH$_2$—) (E) | 92–100 |
| (CH$_3$)(CF$_3$)C=CH(CH$_2$—) (E) | 129–131 |
| (CH$_3$OCH$_2$)(CH$_3$)C=CH(CH$_2$—) (E) | 106–107.5 |
| CH$_3$ | 161.5–163 |
| n-C$_3$H$_7$ | 98–98.5 |
| (CH$_3$)$_3$C— | 200–203 |
| ((CH$_3$)$_2$NCH$_2$)(CH$_3$)C=CH(CH$_2$—) (E) | yellow oil |
| (CH$_3$CH$_2$)(CH$_3$)C=CH(CH$_2$—) (Z) | 121–125 |
| (CH$_3$CH$_2$)(CH$_3$)C=CH(CH$_2$—) (E) | 100–104 |
| (CH$_3$)(FCH$_2$)C=CH(CH$_2$—) (Z) | 138–140 |

EXAMPLE 2

Bioassay for relative cytokinin activity using the cucumber cotyledon test

The compounds of this invention possess plant hormone activity of the class referred to as cytokinins. In view of this, the relative activity of these compounds is determined by a modification of the cucumber cotyledon greening bioassay (Fletcher et al. Plant Physiology (1982) 69:695-77).

Cucumber seeds (Cucumis sativa var. National Pickling) are germinated in vermiculite in the dark at 300° C. for 6 days. The cotyledons are subsequently excised under a dim green safelight and placed abaxial side up in 10×100 cm petri dishes at 8 pairs of cotyledons per dish. The dishes also contain three layers of Whatman No.1 filter paper and 10 mls of test solution. The dishes with cotyledons are returned to the dark at 30° C. for about 18 hours. Thereafter the dishes are placed under fluorescent light at about 12μw per square cm for 3 hours at 25° C. The cotyledons are then blotted and placed in 5 ml of dimethylformamide overnight and at 40° C. to extract the chlorophyll. The leachate is then analyzed for absorbance at 663 nanometers by spectrophotometry (Moran and Porath Plant Physical (1980) 65:478-9) to determine relative chlorophyll biosynthesis. The cotyledons are then measured for area by using a sensitive leaf area meter. These two parameters, chlorophyll synthesis and enhanced expansion of the cotyledons are used as a measure of relative cytokinin activity. The test solutions typically contain between 0.06 and 64 ppm of test compound, up to 1.3% acetone, and 40 mM KCl. The amount of compound is varied in order to determine the dose at which there is achieved a response which is 50% of the maximum possible enhancement, as judged by a standard. This is termed the 50% effective dose or ED50 (Table). The compound is judged as inactive if the amount required is more than 200 ppm. Date obtained are reported in Table below.

TABLE II

Bioassay For Cytokinin Activity Using the Cucumber Cotyledon Test. Compounds Evaluated Have The Structure:

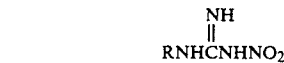

RNHCNHNO$_2$ (NH)

| R | ED$_{50}$, ppm |
|---|---|
| HOOC—CH(NH$_2$)(CH$_2$)$_3$— | 31 |
| (CH$_3$)$_3$C— | 113 |
| | 31 |
| (CH$_3$)$_2$C=CHCH$_2$— | 3.8 |
| n-C$_5$H$_{11}$— | 31 |
| CH$_2$=CHCH$_2$— | 22 |
| C$_2$H$_5$OCH$_2$CH$_2$— | 113 |
| (CH$_3$)$_2$CHCH$_2$CH$_2$— | 64 |
| ClC(CH$_3$)=CHCH$_2$— (Z) | 1.0 |
| n-C$_4$H$_9$— | 31 |
| CH$_3$OCH$_2$CH(CH$_3$)— | 113 |
| (CH$_3$)$_2$CH— | 45 |
| C$_2$H$_5$C(CH$_3$)$_2$— | 22 |
| CH$_2$=CHC(CH$_3$)$_2$— | 157 |

TABLE II-continued

Bioassay For Cytokinin Activity Using the
Cucumber Cotyledon Test, Compounds Evaluated
Have The Structure:

$$RNHCNHNO_2$$
$$\parallel$$
$$NH$$

| R | $ED_{50}$, ppm |
|---|---|
| $HOCH_2\overset{CH_3}{\underset{|}{C}}HCH_2CH_2-$ | 14 |
| $HOCH_2CH_2CH_2CH_2-$ | 113 |
| $(Cl)_2C=CHCH_2CH_2-$ | 11 |
| $\begin{array}{c}HOCH_2\\ \diagdown\\ \diagup\\ CH_3\end{array}C=CH-CH_2-$ (E) | 2.5 |

EXAMPLE 3

Definitive Cytokinin Activity in the Soybean Callus Culture Bioassay

Soybean callus cultures (from *Glycine max* CV. Acme) are subdivided into smaller callus pieces each weighing about 80 mg each. These pieces are placed on 50 ml of agar containing nutrient medium from which the usual growth supporting cytokinin hormone has been deleted. Without cytokinin hormone, the callus tissue will not divide and grow. Any compound which can provide for growth of the callus under these circumstances is by definition a cytokinin. The test is thus definitive and diagnostic. Different flasks of the nutrient medium are therefore supplemented with either the known cytokinin $N^6$-benzyladenine as a standard or with the indicated test compound. After 6 weeks of axenic culture, the callus pieces are weighed, then oven dried and weighed again, such that the amount of callus growth is determined as a function of increased tissue weight. The optimum concentration of the standard, $N^6$benzyladenine, is $10^{-6}M$ with $10^{-4}M$ giving a supraoptimal effect whereby the beneficial effect was negated. The compound 1-(3-methyl-2-butenyl)-3-nitroguanidine is extremely active at $10^{-4}M$ as a cytokinin in this test. Data obtained are reported in Table III below.

TABLE III

Cytokinin Activity of Test Compound in Soybean Callus Growth Test

| Treatment* | mg per 3 pieces | |
|---|---|---|
| | Callus Fresh Weight | Callus Dry Weight |
| No supplement | 283 ± 99 | 22.2 ± 9 |
| 1-(3-methyl-2-butenyl)-3-nitro-guanidine $10^{-4}$ m | 5324 ± 1148 | 410 ± 87 |
| $N^6$-benzyladenine $10^{-6}$ M | 5826 ± 1110 | 351 ± 63 |
| $N^6$benzyladenine, $10^{-4}$ M | 434 ± 193 | 28 ± 5 |

*Initial fresh weight was 240 g; 3 flasks were used per treatment

EXAMPLE 4

Antagonism of Cytokinin Activity By 7-(Isopentylamine)-3-methyl-1H-Pyrazolopyrimidine Using the Cucumber Cotyledon Bioassay The above compound is a known (Hecht el al.) Biochemistry 10:4224 (1971) antagonist of the activity of cytokinins such as the natural cytokinin 6-(-3-methyl2-butenylamino)purine (2iP). For example 0.003 $\mu M$ 2iP is required for maximum growth of tobacco callus tissue cultures. The antagonist decreases this effect in the range of 0.1 $\mu M$ (detectable) to 0.73 $\mu M$ (lethal). (Ref. Skoog et al. Phytochemistry 12:25-37 (1973)).

The antagonist also prevents the response of cucumber cotyledons to the known synthetic cytokinin $N^6$-benzyladenine, indicating that it is also an antagonist of cytokinin in the chlorophyll-synthesis response of the cucumber bioassay. Test solutions are prepared to contain a test compound in both the presence and absence of the antagonist. The cytokinin antagonist is able to fully prevent the enhancement of chlorophyll synthesis in the cucumber cotyledon test (Table). Data obtained are reported in Table IV below.

TABLE IV

Antagonism of 1-(3-methyl-2-butenyl)-3-nitroguanidine By a Cytokinin Antagonist In the Cucumber Cotyledon Bioassay

| Treatment | | | Chlorophyll Increase, |
|---|---|---|---|
| Test Compound | Antagonist | Relative Chlorophyll | % of Maximum |
| A | | | |
| $H_2O$ | None | 370 | 0 |
| $H_2O$ | 10 ppm | 415 | 9.3 |
| $N^6$-benzylamino-purine, 0.1 ppm | None | 853 | 100 |
| $N^6$-benzylamino-purine, 0.1 ppm | 10 ppm | 460 | 18.7 |
| B | | | |
| $H_2O$ | None | 443 | 0 |
| $H_2O$ | 10 ppm | 406 | 4.9 |
| 1-(3-methyl-2-butenyl)-3-nitro-guanidine, 20 ppm | None | 1200 | 100 |
| 1-(3-methyl-2-butenyl)-3-nitro-guanidine, 20 ppm | 10 ppm | 388 | −7.3 |

EXAMPLE 5

Efficacy of the use of guanidine compounds for assisting in stimulation of callus growth in habituated callus tissue A specialized callus tissue (*Nicotiana tabacum* A21-1OH) which was known to be unique in that it had been selected to no longer require cytokinins for callus to grow (this condition is known as "habituated") as long as 2 ppm naphthalene acetic acid was present in the medium, is transferred to flasks of basal media containing mineral salts based on the formulation of Murashige and Skoog, *Physiologia Plantarum* 15:473-497 (1962), and containing 100 mg per liter of i-inositol, 0.4 mg per liter of thiamine.HCl, and 3% sucrose (Huang, L.C. and T. Murashige 1976, TCA manual 3(1):539-548) as well as 0.9% to 0.95% Difco ® agar. The pH of the medium is adjusted to pH 5.8.

For purposes of demonstration the efficacy of use of the guanidine compounds, the basal medium is also supplemented with only 0.02 ppm naphthalene acetic acid (i.e., 1% of the usual level). Test solutions are added from 5000 ppm stock solutions in ethanol and the stimulation of callus growth determined by the increase in fresh weight per treatment (per flask) in grams and by chlorophyll production rated as indicated in the rating system below. (No shoot regeneration can occur in this line due to the length of time (>4 years) it has been maintained in culture.)

Chlorophyll Production Rating System

| Chlorophyll Production Rating System | |
| --- | --- |
| − | None |
| + | Slight |
| ++ | Moderate |
| +++ | Very Good |

The results of these experiments are summarized in Table V below. These results demonstrate
1. the efficacy of the use of the alkenylnitroguanidines of the invention for assisting in callus multiplication and chlorophyll production, and
2. that the use of these compounds is unique in comparison to kinetin, a cytokinin which is ineffective in this system due to the resuction of the auxin level.

TABLE V

Stimulation of Callus Growth From A Habituated line of *Nicotiana tabacum*

| Treatment | Molar Concentration | Callus Growth | |
| --- | --- | --- | --- |
| | | Fresh weight, grams per flask | Chlorophyll production |
| None | — | 0.6 | — |
| Kinetin (standard) | $10^{-7}$ | 0.2 | — |
| | $10^{-6}$ | 0.3 | — |
| | $10^{-5}$ | 0.8 | — |

TABLE V-continued

Stimulation of Callus Growth From A Habituated line of *Nicotiana tabacum*

| Treatment | Molar Concentration | Callus Growth | |
| --- | --- | --- | --- |
| | | Fresh weight, grams per flask | Chlorophyll production |
| 1-(3-methyl-2-butenyl)-3-nitro-guanidine | $10^{-4}$ | 1.4 | — |
| | $10^{-4}$ | 2.9 | ++ |

What is claimed is:

1. A method for inhibiting deterioration of fresh, leafy vegetables, ornamental foliage and fresh, green, newly harvested livestock feed, comprising applying thereto a preservative amount of a substituted nitroguanidine compound, wherein the nitroguanidine compound is

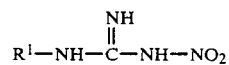

wherein
$R^1$ is $C_1$–$C_6$ alkyl, optionally substituted with from one to three OH, halogen or $C_1$–$C_3$ alkoxy groups; $C_2$–$C_6$ alkenyl optionally substituted with from one to three OH, halogen or $C_1$–$C_3$ alkoxy groups or $C_2$–$C_6$ alkynl, optionally substituted with from one to three OH, halogen or $C_1$–$C_3$ alkoxy groups; or the salts, geometric isoners, optical isomers or tautomers thereof.

2. The method according to claim 1, wherein said nitroguanidine compound is applied as a dilute formulation containing from about 0.01 to 1000 ppm of said nitroguanidine compound.

3. The method according to claim 2, wherein said compound is 1-(3-methyl-2-butenyl)-3-nitroguanidine.

4. The method according to claim 1, wherein said compound is 1-(3-chloro-2-butenyl)-3 -nitroguanidine.

* * * * *